United States Patent [19]
Ward et al.

[11] Patent Number: 5,741,668
[45] Date of Patent: Apr. 21, 1998

[54] EXPRESSION OF A GENE FOR A MODIFIED GREEN-FLUORESCENT PROTEIN

[75] Inventors: William W. Ward, Metuchen, N.J.; Martin Chalfie, New York, N.Y.

[73] Assignees: Rutgers, the State University of New Jersey, Piscataway, N.J.; The Trustees of Columbia University in the City of NY, New York, N.Y.

[21] Appl. No.: 452,295

[22] Filed: May 26, 1995

Related U.S. Application Data

[62] Division of Ser. No. 192,158, Feb. 4, 1994, abandoned.

[51] Int. Cl.[6] .................... C12P 21/00; C12N 15/63; C07H 21/04
[52] U.S. Cl. .................. 435/69.1; 435/8; 435/71.1; 435/172.3; 435/189; 435/252.3; 435/252.33; 435/320.1; 536/23.2
[58] Field of Search .................. 435/69.1, 8, 71.1, 435/172.3, 252.3, 252.33, 320.1, 189

[56] References Cited

U.S. PATENT DOCUMENTS

| | | | |
|---|---|---|---|
| 5,023,181 | 6/1991 | Inouye | 435/189 |
| 5,093,240 | 3/1992 | Inouye et al. | 435/69.1 |
| 5,162,227 | 11/1992 | Cormier | 435/252.33 |
| 5,360,728 | 11/1994 | Prasher et al | 435/189 |
| 5,422,266 | 6/1995 | Cormier et al. | 435/252.3 |
| 5,491,084 | 2/1996 | Chalfie et al. | 435/189 |
| 5,541,309 | 7/1996 | Prasher | 536/23.2 |

OTHER PUBLICATIONS

Prasher et al., Gene 111:229–233, 1992.

*Primary Examiner*—W. Gary Jones
*Assistant Examiner*—Paul B. Tran
*Attorney, Agent, or Firm*—Omri M. Behr, Esq.

[57] ABSTRACT

A pre-coelenterazine peptide comprising a modified *A. victoria* GFP having an amino acid sequence in which $Ser^{65}$ is replaced with Tyr. There is further provided a polynucleotide encoding the pre-coelenterazine peptide, allowing synthesis of large, pure amounts of coelenterazine.

7 Claims, 3 Drawing Sheets

FIGURE 1

The amino acid sequence of a pre-coelenterazine peptide:

```
Xaa Ser Lys Gly Glu Glu Leu Phe Thr Gly Val Val Pro Ile Leu Val
 1           5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
    50                  55                  60

Tyr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

FIG. 2

The nucleotide sequence of cDNA segment gfp(C197A) encoding the pre-coelenterazine peptide of Figure 1:

```
ATGGCTAGCA AAGGAGAAGA ACTTTTCACT GGAGTTGTCC CAATTCTTGT TGAATTAGAT      60

GGTGATGTTA ATGGGCACAA ATTTTCTGTC AGTGGAGAGG GTGAAGGTGA TGCAACATAC     120

GGAAAACTTA CCCTTAAATT TATTTGCACT ACTGGAAAAC TACCTGTTCC ATGGCCAACA     180

CTTGTCACTA CTTTCTATTA TGGTGTTCAA TGCTTTTCAA GATACCCAGA TCATATGAAA     240

CAGCATGACT TTTTCAAGAG TGCCATGCCC GAAGGTTATG TACAGGAAAG AACTATATTT     300

TTCAAAGATG ACGGGAACTA CAAGACACGT GCTGAAGTCA AGTTTGAAGG TGATACCCTT     360

GTTAATAGAA TCGAGTTAAA AGGTATTGAT TTTAAAGAAG ATGGAAACAT TCTTGGACAC     420

AAATTGGAAT ACAACTATAA CTCACACAAT GTATACATCA TGGCAGACAA ACAAAAGAAT     480

GGAATCAAAG TTAACTTCAA AATTAGACAC AACATTGAAG ATGGAAGCGT TCAACTAGCA     540

GACCATTATC AACAAAATAC TCCAATTGGC GATGGCCCTG TCCTTTTACC AGACAACCAT     600

TACCTGTCCA CACAATCTGC CCTTTCGAAA GATCCCAACG AAAAGAGAGA CCACATGGTC     660

CTTCTTGAGT TTGTAACAGC TGCTGGGATT ACACATGGCA TGGATGAACT ATACAAATAA     720

ATGTCCAGAC TTCCAATTGA CACTAAAGTG TCCGAACAAT TACTAAAATC TCAGGGTTCC     780

TGGTTAAATT CAGGCTGAGA TATTATTTAT ATATTTATAG ATTCATTAAA ATTGTATGAA     840

TAATTTATTG ATGTTATTGA TAGAGGTTAT TTTCTTATTA AACAGGCTAC TTGGAGTGTA     900

TTCTTAATTC TATATTAATT ACAATTTGAT TTGACTTGCT CAAA                     944
```

FIG. 3

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 238 amino acids
        ( B ) TYPE: amino acid
        ( D ) TOPOLOGY: unknown     ( i x ) FEATURE:
        ( A ) NAME/KEY: Protein
        ( B ) LOCATION: one-of(1)

( D ) OTHER INFORMATION: /note= "Residue 1 Xaa = Methionyl- alanine"

( x i ) SEQUENCE DESCRIPTION: SEQ ID NO:1:

```
Xaa  Ser  Lys  Gly  Glu  Glu  Leu  Phe  Thr  Gly  Val  Val  Pro  Ile  Leu  Val
1                  5                        10                       15

Glu  Leu  Asp  Gly  Asp  Val  Asn  Gly  His  Lys  Phe  Ser  Val  Ser  Gly  Glu
               20                   25                       30

Gly  Glu  Gly  Asp  Ala  Thr  Tyr  Gly  Lys  Leu  Thr  Leu  Lys  Phe  Ile  Cys
          35                        40                       45

Thr  Thr  Gly  Lys  Leu  Pro  Val  Pro  Trp  Pro  Thr  Leu  Val  Thr  Thr  Phe
     50                        55                       60

Tyr  Tyr  Gly  Val  Gln  Cys  Phe  Ser  Arg  Tyr  Pro  Asp  His  Met  Lys  Gln
65                       70                   75                            80

His  Asp  Phe  Phe  Lys  Ser  Ala  Met  Pro  Glu  Gly  Tyr  Val  Gln  Glu  Arg
                85                        90                            95

Thr  Ile  Phe  Tyr  Lys  Asp  Asp  Gly  Asn  Tyr  Lys  Ser  Arg  Ala  Glu  Val
               100                       105                       110

Lys  Phe  Glu  Gly  Asp  Thr  Leu  Val  Asn  Arg  Ile  Glu  Leu  Lys  Gly  Ile
          115                       120                       125

Asp  Phe  Lys  Glu  Asp  Gly  Asn  Ile  Leu  Gly  His  Lys  Met  Glu  Tyr  Asn
     130                       135                       140

Tyr  Asn  Ser  His  Asn  Val  Tyr  Ile  Met  Ala  Asp  Lys  Gln  Lys  Asn  Gly
145                      150                       155                       160

Ile  Lys  Val  Asn  Phe  Lys  Ile  Arg  His  Asn  Ile  Glu  Asp  Gly  Ser  Val
                165                       170                       175

Gln  Leu  Ala  Asp  His  Tyr  Gln  Gln  Asn  Thr  Pro  Ile  Gly  Asp  Gly  Pro
               180                       185                       190

Val  Leu  Leu  Pro  Asp  Asn  His  Tyr  Leu  Ser  Thr  Gln  Ser  Ala  Leu  Ser
          195                       200                       205

Lys  Asp  Pro  Asn  Glu  Lys  Arg  Asp  His  Met  Ile  Leu  Leu  Glu  Phe  Val
     210                       215                       220

Thr  Ala  Ala  Gly  Ile  Thr  His  Gly  Met  Asp  Glu  Leu  Tyr  Lys
225                       230                       235
```

( 2 ) INFORMATION FOR SEQ ID NO:2:

( i ) SEQUENCE CHARACTERISTICS:
( A ) LENGTH: 944 bases
( B ) TYPE: nucleic acid
( C ) STRANDEDNESS: both
( D ) TOPOLOGY: linear ( i i ) MOLECULE TYPE: cDNA ( x i ) SEQUENCE DESCRIPTION: SEQ ID NO:2:

```
ATGGCTAGCA  AAGGAGAAGA  ACTTTTCACT  GGAGTTGTCC  CAATTCTTGT  TGAATTAGAT    60

GGTGATGTTA  ATGGGCACAA  ATTTTCTGTC  AGTGGAGAGG  GTGAAGGTGA  TGCAACATAC   120

GGAAAACTTA  CCCTTAAATT  TATTTGCACT  ACTGGAAAAC  TACCTGTTCC  ATGGCCAACA   180

CTTGTCACTA  CTTTCTATTA  TGGTGTTCAA  TGCTTTTCAA  GATACCCAGA  TCATATGAAA   240

CAGCATGACT  TTTTCAAGAG  TGCCATGCCC  GAAGGTTATG  TACAGGAAAG  AACTATATTT   300

TTCAAAGATG  ACGGGAACTA  CAAGACACGT  GCTGAAGTCA  AGTTTGAAGG  TGATACCCTT   360

GTTAATAGAA  TCGAGTTAAA  AGGTATTGAT  TTTAAAGAAG  ATGGAAACAT  TCTTGGACAC   420

AAATTGGAAT  ACAACTATAA  CTCACACAAT  GTATACATCA  TGGCAGACAA  ACAAAAGAAT   480

GGAATCAAAG  TTAACTTCAA  AATTAGACAC  AACATTGAAG  ATGGAAGCGT  TCAACTAGCA   540
```

```
GACCATTATC  AACAAAATAC  TCCAATTGGC  GATGGCCCTG  TCCTTTTACC  AGACAACCAT     600

TACCTGTCCA  CACAATCTGC  CCTTTCGAAA  GATCCCAACG  AAAAGAGAGA  CCACATGGTC     660

CTTCTTGAGT  TTGTAACAGC  TGCTGGGATT  ACACATGGCA  TGGATGAACT  ATACAAATAA     720

ATGTCCAGAC  TTCCAATTGA  CACTAAAGTG  TCCGAACAAT  TACTAAAATC  TCAGGGTTCC     780

TGGTTAAATT  CAGGCTGAGA  TATTATTTAT  ATATTTATAG  ATTCATTAAA  ATTGTATGAA     840

TAATTTATTG  ATGTTATTGA  TAGAGGTTAT  TTTCTTATTA  AACAGGCTAC  TTGGAGTGTA     900

TTCTTAATTC  TATATTAATT  ACAATTTGAT  TTGACTTGCT  CAAA                       944
```

( 2 ) INFORMATION FOR SEQ ID NO:3:

( i ) SEQUENCE CHARACTERISTICS:
        ( A ) LENGTH: 18 bases
        ( B ) TYPE: nucleic acid
        ( C ) STRANDEDNESS: both
        ( D ) TOPOLOGY: linear     ( i i ) MOLECULE TYPE: cDNA     ( x i ) SEQUENCE DESCRIPTION: SEQ ID NO:3:

```
TTCTATTATG  GTGTTCAA                                                        18
```

( 2 ) INFORMATION FOR SEQ ID NO:4:

( i ) SEQUENCE CHARACTERISTICS:
        ( A ) LENGTH: 40 bases
        ( B ) TYPE: nucleic acid
        ( C ) STRANDEDNESS: both
        ( D ) TOPOLOGY: unknown     ( i i ) MOLECULE TYPE: cDNA     ( x i ) SEQUENCE DESCRIPTION: SEQ ID NO:4:

```
CCTGTTCCAT  GGCCAACACT  TGTCACTACT  TTCTATTATG                             40
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:5:

```
Phe  Ser  Tyr  Gly  Val  Gln
1               5
```

EXPRESSION OF A GENE FOR A MODIFIED GREEN-FLUORESCENT PROTEIN

This application is a division of application Ser. No. 08/192,158, filed Feb. 4, 1994 now abandoned.

FIELD OF THE INVENTION

This invention concerns a method for synthesizing a bioluminescent compound, namely coelenterazine; a polynucleotide which encodes for a pre-peptide of coelenterazine; organisms transformed with this polynucleotide; and an improved assay for mutagenesis.

BACKGROUND OF THE INVENTION

For some years now, it has been appreciated that bioluminescence offers a useful indicative tool in diagnostic assays. The genes for the bacterial lux system have been introduced into a number of non-bioluminescent species; similarly, the firefly luciferase gene has been expressed in *E. coli*, tuberculosis bacilli and tobacco plants grown in an ambient medium containing firefly luciferin. However, as explained below, due to the biochemical prerequisites of most bioluminescing systems, as well as to the limited availability, the structural complexity and the unknown route of biosynthesis of particular bioluminescent molecules, investigators have generally been unable to employ bioluminescing compounds in many assays, particularly assays for gene expression in living cells. Due to the present invention, these difficulties and limitations have been overcome and broader application of the coelenterate bioluminescent system is now feasible.

The general chemical reaction underlying the phenomenon of bioluminescence is the oxidation of a substrate ("luciferin") by an enzyme ("luciferase"), usually in the presence of oxygen. An intermediate, energized "oxyluciferin*," is formed during this oxidation, which, in proceeding to the oxidized form ("oxyluciferin"), releases light. (Bioluminescent bacteria do not employ a luciferin unique to bioluminescence reaction, but the ubiquitous electron transfer agent $FMNH_2$, i.e., riboflavine-5-phosphate.)

It should be noted that the terms "luciferin" and "luciferase" are non-specific: they are used in the literature to refer to the bioluminescing enzyme and substrate of nearly all bioluminescing organisms. The specific luciferins found in nature however vary extensively. For example, the luciferin of the firefly, the ostracod Cypridina and the coelenterates (a group of marine organisms including the jellyfish and the sea pansy) are clearly distinct molecules, as shown in Formulae I, II and III:

Formula I

Formula II

Formula III

These three compounds are usually termed firefly luciferin, Cypridina luciferin and coelenterate-type luciferin (or "coelenterazine") respectively to avoid confusion.

Generally, there is little cross reaction between the luciferase of one species and the luciferin of another: firefly luciferase will not oxidize either the Cypridina or coelenterate-type luciferin. Among members of an animal phylum however, (e.g., among coelenterates), cross-reactions are found: thus the combination of *A. victoria* coelenterazine with *Renilla reniformis* luciferase does generate bioluminescence. This occurs because all coelenterates have coelenterazine as their luciferin.

Coelenterazine (or 3,7-dihydro-2-methyl-6-(p-hydroxyphenyl)-8-obenzylimidazo [1,2-a]pyrazin-3-one, Hori and Cormier, *Proc. Nat. Acad. Sci.* 70, No. 1, 120–123 (1973) releases blue light across a broad range peaking at 480 nm upon oxidation by luciferase in vitro. However, the bioluminescence of coelenterates in vivo is not blue, but green, peaking at 510 nm. This is due to the in vivo interaction between the luciferin and "green-fluorescent protein" (hereinafter "GFP"). GFP is a polypeptide derived from an apo-peptide with 238 amino acids and a molecular weight of approximately 27,000. GFP contains a chromophore having the structure shown in Formula IV:

Formula IV

Cody et al., *Bioch*, 38 1212–1218 (1993). Energy transfer from coelenterazine to GFP is believed to excite GFP in vivo, resulting in green bioluminescence identical to the fluorescence emission spectrum of GFP.

Recombinant DNA techniques have assisted in the elucidation of bioluminescent systems, and have enabled investigators to introduce some bioluminescent compounds into assays to provide a convenient, conspicuous indicator. Thus, the lux genes of bacteria have been incorporated into several other species of bacteria, which have then been employed in a wide range of assays. These are discussed in Gould *Anal. Bioch* 175, 5–13, incorporated herein by reference; Stewart and Williams, *J. Gen. Mcbio.*, 138 1289–1300 (1992), incorporated herein by reference; Stewart and Williams, *ASM News*, 59, No. 5, 241–246 (1993), incorporated herein by reference; and Hill et al., *Biotechn. App. Bioch.* 17, 3–14 (1993), incorporated herein by reference. Also, the firefly luciferase gene has been incorporated into *E. coli*, as described in Lee et al., *Anal. Chem.* 64, 175–1759 (1992), incorporated herein by reference. When a mutagen induces a lysogenic bacteriophage carried by these *E. coli*, the bacteria lyse. Lysis releases the firefly luciferase into a medium containing firefly luciferin, and a flash of light results.

These assays enjoy the advantages of accuracy and great sensitivity. The accuracy results from the highly specific interaction between firefly luciferase and its luciferin, keeping the number of false positive indications low. The sensitivity of these assays is due to the great sensitivity of light sensing equipment and photomultipliers. When properly designed, such assays may additionally offer a quantitative relationship between the level of light released and the phenomenon being measured.

However, these assays are also limited by the need of most bioluminescent compounds to have present an exogenously added co-factor. Without the appropriate co-factor, the system will not bioluminesce. Thus, firefly luciferase will only oxidize firefly luciferin in the presence of ATP and bacterial luciferase only oxidizes $FMNH_2$ if organic aldehydes are also present.

By contrast, coelenterate luciferase and coelenterazine require only oxygen in order to generate light at 480 nm. Despite this advantage, the coelenterate bioluminescence system has not been extensively employed in assays, primarily due to the great difficulty and expense of isolating significant amounts of the compound. Coelenterazine is present in bioluminescing organisms at exceedingly low levels: forty thousand sea pansies (*Renilla reniformis*) must be harvested to collect 0.5 mg of coelenterazine; similarly, six thousand sea pansies yield only a few milligrams of Renilla luciferase. "General Aspects of Bioluminescence," Ward, 321–358, at 344 in *Chemi- and Bioluminescence*, J. G. Burr, Ed., Marcel Dekker, Inc., 1985. Furthermore, the chemical instability of the compound limits its half life in aqueous systems to one to two hours.

Although synthetic coelenterazine is available commercially (from London Diagnostics, Eden Prairie, Minn.), it too is also quite expensive as its synthesis requires numerous complex organic reactions. Recombinant DNA techniques to date have provided no assistance, since the natural route of coelenterazine biosynthesis, and indeed that of most luciferins, is unknown.

Some investigators have theorized biosynthetic pathways for coelenterazine. McCapra and Perring, 359–386, at 371, in *Chemi- and Bioluminescence*, J. G. Burr, supra, noted some structural similarities between coelenterazine and the tripeptide tyrosyl-tyrosyl-phenylalanine, and expressed a belief that coelenterazine is derivable from this tripeptide. Elsewhere, McCapra alone pointed out structural similarity between Cypridina luciferin (which shares the fused imidazo-pyrazine ring of coelenterazine) and the tripeptide tryptophanyl-isoleucyl-arginine, synthesized the Cypridina luciferin from a dehydrodipeptide in *JCS Chem. Comm.* 1972, "Cyclisation of a Dehydropeptide Derivative: a Model for Cypridina Luciferin Biosynthesis" 894–895. Observing a possible connection between a tripeptide and luciferin, in *FEBS Lett.* 104, 1979, pp. 220–222, Shimomura stated: "Partial similarity between structure B [the proposed GFP chromophore] and the structure of coelenterazine may suggest a biogeneric significance." Ward similarly observed in *Chemi- and Bioluminescence* J. G. Burr, supra, at p. 329 that in view of the chemical similarities between Cypridina luciferin and coelenterazine, it was intriguing to speculate that coelenterate-type luciferin and the GFP chromphore may be produced by a common biosynthetic mechanism involving post-translational protein modification (i.e., ring formation) followed by excision of the chromophore in the case of luciferin synthesis.

Despite the references to tripeptides in the biosynthesis of coelenterazine, it has hitherto generally been believed by investigators that coelenterazine was not generated through ribosomal peptide synthesis. Rather, due to the compound's structural complexity, investigators expected coelenterazine was synthesized non-ribosomally, in the manner of γ-glutamylcysteinylglycine ("glutathione", the natural antioxidant which forms 5-oxoproline in the γ-glutamyl cycle) or gramicidin. *Biochemistry*, Voet and Voet, John Wiley & Sons, pp. 709–711, 941–942; and *Biochemistry*, Zubay, 2d Ed., Macmillan Publishing Company, p. 796. McCapra and Perring's observations above are believed to have been directed to possible laboratory synthesis routes for the luciferins discussed; for they flatly state that [n]one of the chemical syntheses [of luciferins] are amino acid based . . . . Id., at 371. Instead, it was hypothesized that different organisms might possess specific genes, namely a series of cooperating enzymes, for the synthesis of coelenterazine, J. W. Hastings, *J. Mol. Evol.* 19, 309–321 (1983); and that coelenterazine synthesis would occur in vivo via a sequence of enzymatic or chemical reactions, McCapra and Perring, Id., at 375–376.

This lack of knowledge about the biosynthesic pathways for luciferins highlights a further problem generally suffered to date by assays employing transgenic bioluminescent organisms; i.e., that bioluminescence will not be exhibited by living cells (aside from bacteria transformed with the lux genes) unless the co-factor and luciferin compatible with that luciferase are able to diffuse through a cell membrane. The diffusability of firefly luciferin was demonstrated in Ow et al., *Science* 234, 856–859 (1986), where tobacco plants grown from cells transformed with the firefly luciferase gene were exposed to a liquid medium containing firefly luciferin. The plants exhibited bioluminescence primarily along their major veins.

In summary, until very recently, bioluminescent assays have employed luciferin systems requiring co-factors. In these assays, bioluminescence was only observed if the luciferin and co-factor employed were able to diffuse through cell membranes. Where little or no diffusion occurred, bioluminescence was only observed by providing a luciferin in the growth medium and lysing cells expressing a luciferase gene. If assays employed cells which permitted only low rates of luciferin and co-factor diffusion, these assays could not be useful tools in investigating living cells expressing a luciferase peptide. Consequently, bioluminescence has not provided in conventional assays a useful indicator for gene expression in living cells.

Recently however, the requirement for a diffusible luciferin and co-factors has been obviated in U.S. patent application Ser. No. 08/119,678, filed Sep. 10, 1993 by Chalfie et al. (hereinafter "Chalfie et al.") This application, which is incorporated herein by reference, describes the synthesis in *E. coli* and *C. elegans* of the GFP of the jellyfish *A. victoria*. These cells were transformed with a cDNA for the 238 amino acid apo-GFP. This apo-protein of GFP was expressed in those cells in the absence of other jellyfish gene products. Furthermore, this apo-peptide was found to undergo post-trans-lational modification at its residues 64 through 69 to form the GFP chromophore (of Formula IV above). The resulting GFP exhibits the characteristic green fluorescence at 510 nm upon irradiation with blue or UV light. Thus, cells transformed with the cDNA for apo-GFP may be tested for GFP expression simply by irradiation with blue or UV light; no cell lysis is required to detect fluorescence. Moreover, one need not provide a co-factor or even a luciferin.

SUMMARY OF THE INVENTION

Applicants have discovered that by modifying the cDNA for the apo-peptide of *A. victoria* GFP (described in U.S. Pat. No. 5,431,084, a heretofore unexpected pre-coelenterazine peptide is synthesized. Polynucleotides encoding this prepeptide allow synthesis of large, pure amounts of coelenterazine and enable numerous methods for imparting bioluminescence to organisms under a variety of conditions.

The discovery that GFP may by slight modification be altered to a pre-coelenterazine peptide, and that polynucleotides encoding the apo-peptide for GFP could be modified to encode for the pre-coelenterazine peptide was wholly unforeseen. There existed no earlier indication that coelenterazine results from post-translational modification of any peptide; or that coelenterazine is or could be genetically encoded. Nor was there any clear indication that GFP and coelenterazine might share a common or related precursor.

Moreover, the steps believed to be involved in coelenterazine formation from the pre-coelenterazine peptide are substantially different from those believed to occur in formation of the GFP chromophore. Investigators have proposed a mechanism for the formation of the chromophore in GFP. In this proposed mechanism, $Tyr^{66}$ in GFP is dehydrogenated, and later cyclizes along with its upstream neighbor $Ser^{65}$, as well as its downstream neighbor $Gly^{67}$ to form the imidazole ring chromophore, as described in Cody et al, supra. These steps fail to foreshadow the dehydrogenations and cyclization believed to occur in the pre-coelenterazine peptide.

Without in any way limiting the invention, Applicants believe that pre-coelenterazine is transformed into coelenterazine by the dehydrogenation of $Tyr^{66}$ and/or its upstream neighbor $Tyr^{65}$ (which replaces the $Ser^{65}$ of GFP). Either one Tyr residue and one dehydroTyr residue (or both dehydroTyr residues) then cyclize with their further upstream neighbor $Phe^{64}$. In this cyclization, the peptide bond between residues 63 and 64 and that between residues 66 and 67 are broken; cyclization thus brings about excision of coelenterazine from the peptide.

Nothing in the Cody et el. mechanism of GFP chromophore formation indicates that the replacement of $Ser^{65}$ with $Tyr^{65}$ in the modified GFP would lead to dehydrogenation of both $Tyr^{66}$ and $Tyr^{65}$. Nor is there any indication that this replacement would lead to an upstream-shift of the residues which cyclize into a ring; or in two fused rings being formed in place of one: in GFP, residues 65, 66 and 67 cyclizing into a pyrazole ring, while in pre-coelenterazine, residues 64, 65 and 66 cyclize into a fused imadazo-pyrazine ring.

The following improvements are a result of Applicants' surprising discovery. The first embodiment of the invention is a pre-coelenterazine peptide comprising the modified amino acid sequence of an *A. victoria* GFP in which $R^{65}$ is Tyr. In these peptides, several amino acid residues may vary; $R^{80}$ may be Gln or Arg, $R^{100}$ may be Phe or Tyr, $R^{108}$ may be Thr or Ser, $R^{141}$ may be Leu or Met, $R^{172}$ may be Glu or Lys, and $R^{219}$ may be Val or Ile. Regardless of which of the above-identified amino acyl residues is present at residue 80, 100, 108, 141, 172 and 219, the resulting pre-coelenterazine peptide is formed, when generated in vivo or in a cell-free ribosomal system, to yield coelenterazine. One suitable pre-coelenterazine peptide has a modified amino acid sequence of GFP in which $R^{80}$ is Gln, $R^{100}$ is Phe, $R^{108}$ is Thr, $R^{141}$ is Leu, $R^{172}$ is Glu, and $F^{219}$ is Val. In another suitable peptide, $R^{80}$ is Gln, $R^{100}$ is Tyr, $R^{108}$ is Ser, and $R^{141}$ is Met, $R^{172}$ is Glu, and $R^{219}$ is Ile.

These peptides may be synthesized by a suitable method such as by exclusive solid phase techniques, by partial solid-phase techniques, by fragment condensation by classical solution phase synthesis, or by recombinant DNA techniques.

In a second embodiment, the invention provides a polynucleotide comprising one or more sequences of nucleotide bases collectively encoding the modified amino acid sequence of a GFP of *A. victoria* in which $R^{65}$ is Tyr. In these polynucleotides, the nucleotides encoding for several amino residues may vary: $R^{80}$ may be Gln or Arg, $R^{100}$ may be Phe or Tyr, $R^{108}$ may be Thr or Ser, $R^{141}$ may be Leu or Met, $R^{172}$ may be Glu or Lys, and $R^{219}$ may be Val or Ile.

The one or more sequences of bases collectively encoding the pre-coelenterazine peptide in these polynucleotides may be uninterrupted by non-coding sequences. For example, the polynucleotide could suitably be a cDNA encoding for a modified GFP gene of *A. victoria* in which the nucleotides for amino acid 65 have been mutated from TCT to TAT. Such a polynucleotide appears in FIG. 2. This polynucleotide is, in the present invention, denominated gfp(C197A) to indicate the mutation in the cDNA of GFP at nucleotide 197 from C to A.

All of the above polynucleotides may further comprise, 5' of said one or more sequences of bases, one or more appropriate regulatory control sequences which collectively enable expression of said one or more sequences of bases encoding said pre-coelenterazine peptide.

When in an expression vector, the polynucleotide carries one or more appropriate regulatory control sequences, there may further be present one or more further sequences of bases which collectively confer resistance to an antibiotic, when the polynucleotide is expressed in an organism. One suitable expression vector comprises gfp(C197A); another is plasmid TU#132.

There are further embraced in the second embodiment of the invention a polynucleotide comprising one or more sequences of nucleotide bases collectively encoding the amino acid sequence of $R^1$ through $R^{69}$ of said pre-coelenterazine peptide, as well as an oligonucleotide encoding the amino acid sequence of amino acid residues 64 through 69 of a pre-coelenterazine peptide. One such oligonucleotide has the nucleotide sequence TTC TAT TAT GGT GTT CAA SEQ. ID. No. 3.

A third embodiment of the present invention is an organism transformed with a polynucleotide comprising one or more sequences of nucleotide bases collectively encoding the modified amino acid sequence of a GFP of *A. victoria* in which $R^{65}$ is Tyr, $R^{80}$ is Gln or Arg, $R^{100}$ is Phe or Tyr, $R^{108}$ is Thr or Ser, $R^{141}$ is Leu or Met, $R^{172}$ is Glu or Lys, and $R^{219}$ is Val or Ile. Suitable organisms are those which have been transformed with any of the other polynucleotides described above. Transformation of these cells may be performed by techniques well known to persons having skill in the art with appropriate expression vectors, e.g., plasmid TU#132.

In a fourth embodiment, there is provided a method of synthesizing a peptide comprising the modified amino acid sequence of a GFP of *A. victoria* in which $R^{65}$ is Tyr, including those in which, $R^{80}$ is Gln or Arg, $R^{100}$ is Phe or Tyr, $R^{108}$ is Thr or Ser, $R^{141}$ is Leu or Met, $R^{172}$ is Glu or Lys, and $R^{219}$ is Val or Ile. This method comprises incubating a polynucleotide comprising one or more sequences of nucleotide bases collectively encoding an amino acid sequence of such a peptide in the presence of means for effecting expression of the polynucleotide under conditions favorable for the expression of the polynucleotide.

The step of incubating the polynucleotide may be preceded by transforming an organism with the polynucleotide, and in which the means for effecting expression of the polynucleotide is the transformed organism.

In one variant of this method, there is provided a method of synthesizing coelenterazine comprising synthesizing a pre-coelenterazine peptide, and isolating coelenterazine from said means.

Any of the organisms identified above is suitable; transformation may be by any procedures deemed appropriate by those skilled in the art. The step of incubating the poylynucleotide may be performed by culturing the transformed organism for one or more generations under conditions favorable to growth of the transformed organism and to expression of the polynucleotide, and the step of isolating coelenterazine may be performed by lysing the progeny of the cultured transformed organism to form a cell-free extract, and isolating coelenterazine from this extract.

In this method, the means for effecting expression of said polynucleotide may be *E. coli* strain BL21(DE3)Lys S (Studier and Moffat, *J. Mol. Biol.* 189 113 (1986), incorporated herein by reference) transformed with an expression vector comprising, 5' of said one or more sequences of nucleotide bases collectively encoding the amino acid sequence of pre-coelenterazine peptide, one or more appropriate regulatory control sequences which collectively enable expression of said polynucleotide; and one or more sequences of bases which collectively confer resistance to an antibiotic upon an organism. One such transformed *E. coli* is *E. coli* SMC2 (ATCC Accession No. 69553).

Alternatively, the means for effecting expression of said polynucleotide when comprises of RNA may be a cell-free aqueous translation system known to those skilled in the art.

The method may further comprise the step of converting isolated coelenterazine to a stable form, luciferyl sulfate, as for example by incubating isolated coelenterazine with a luciferin sulfokinase. The luciferin sulfokinase may suitably be derived from the organism *Renilla reniformis*.

This embodiment further includes purified coelenterazine and purified luciferyl sulfate synthesized by one of the above methods.

In a fifth embodiment, the invention provides assays employing bioluminescence as an indicator. These assays employ a further polynucleotide having one or more sequences of nucleotide bases collectively encoding the amino acid sequence of a luciferase compatible with coelenterazine. (A luciferase is compatible with coelenterazine if, when combined in an aqueous medium with said coelenterazine, it generates bioluminescence at or about 480 nm.) One such suitable luciferase is that isolated from the sea pansy *Renilla reniformis* and encoded in the polynucleotide disclosed in Lorenz et el., *Proc. Nat. Acad. Sci.*, 8.8, 4438–4442, 1991, incorporated herein by reference. As with the above polynucleotides, the luciferase polynucleotide may further comprise appropriate regulatory sequences and sequences conferring antibiotic resistance, and even the polynucleotide comprising sequences encoding the amino acid sequence of the pre-coelenterazine peptide. In the assays of this embodiment, organisms which do not naturally bioluminesce at 480 nm are transformed with both polynucleotides. Thus, upon expression of the pre-coelenterazine peptide and luciferase genes, the organisms exhibit bioluminescence at or about 480 nm. These assays may be employed for a variety of uses, as for example to measure the expression of certain genes or for oncogene induction.

These assays may be of the type described for detecting the presence of different molecules in biological samples and for localizing a protein of interest in a cell, both described in Chalfie et al, supra.

In a sixth embodiment, the invention provides an organism transformed with two polynucleotides. The first polynucleotide comprises one or more sequences of nucleotide bases collectively encoding a pre-coelenterazine peptide comprising a modified *A. victoria* GFP having an amino acid sequence in which $R^{65}$ is Tyr. The second polynucleotide comprises one or more sequences of nucleotide bases collectively encoding an amino acid sequence for a luciferase peptide compatible with coelenterazine. One of the polynucleotides has a mutation which precludes a bioluminescent interaction between their expression products. The mutation is desirably reversible upon exposure of the transformed organism to a mutagen; reversion of the mutation enables a bioluminescent interaction between the two expression products.

Any of the organisms identified above is suitable; transformation may be by any procedure deemed appropriate by those skilled in the art. The transformed organism may be employed in an assay to detect mutagenesis, as in a modified "Ames test." Ames et al., *Proc. Nat. Acad. Sci.*, 70., 782–786 and 2281–2285 (1973), incorporated herein by reference.

This embodiment further provides a method of detecting mutagenesis caused by a chemical compound suspected of being a mutagen. The method comprises the steps of transforming a population of organisms with both of the first and second polynucleotides described above; growing a culture of said transformed organisms through one or more generations in a nutrient medium comprising said chemical compound; and measuring the bioluminescence of said culture and comparing said bioluminescence to that from a culture of non-transformed mutagenized control organisms.

DETAILED DESCRIPTION OF THE PREFERRED EMBODIMENTS

Abbreviations and Conventions. The usual conventions for indicating polypeptides (written with N-terminal to left, C-terminal to right) and polynucleotides (written 5' to left, 3' to right) are followed herein. The residues of the pre-coelenterazine peptide are numbered according to Prasher, et al., *Gene* 111, 229–233, 1992, (incorporated herein by reference) beginning with $R^1$ at the N-terminal and proceeding sequentially toward the C-terminal, which is $R^{238}$.

Any DNA disclosed as an individual single-stranded DNA also is considered to disclose the double-stranded DNA forming the same, as well as RNA equivalent thereto.

Applicants state at several points herein that methods, techniques, organisms, and various means for carrying out identified procedures, all of which are well known in the art, may suitably be used. This statement is not to be interpreted that every possible alternative means is equally desirable and effective; the choice among these alternative techniques, organisms and combinations thereof is left to the skill and discretion of one skilled in the art. Conversely, Applicants' statements herein that certain specific techniques and organisms may suitably be used is not to be interpreted that these specified techniques or organisms, or certain combinations thereof, are particularly preferred. The identification of these techniques and organisms is merely exemplary.

A. PRE-COELENTERAZINE PEPTIDE

The primary structure of the pre-coelenterazine peptide is substantially based on that of the GFP of *A. victoria* appearing in Prasher et al., supra, except that $Set^{65}$ appearing in the chromogenic sequence of amino acyl residues of apo-GFP, i.e., $Phe^{64}$-$Ser^{65}$-$Tyr^{66}$-$Gly^{67}$-$Val^{68}$-$Gln^{69}$, is replaced by Tyr.

Variations are seen in the amino acid sequence of wild *A. victoria* jellyfish GFP at several residues: $R^{80}$ may be Gin or Arg, $R^{100}$ may be Phe or Tyr, $R^{108}$ may be Thr or Ser, $R^{141}$ may be Leu or Met, $R^{172}$ may be Glu or Lys, and $R^{219}$ may be Val or Ile. These same replacements may be made in the pre-coelenterazine without substantial prejudice. The length of the pre-coelenterazine peptide may also be subject to minor differences in length: i.e., the primary sequence of the peptide may slightly exceed or fall short of 238 amino acyl residues.

This length variation may arise when the peptide is derived from a polypeptide having 5' or 3' termini to which "sticky end" nucleotide sequences have been added by procedures known to persons skilled in the art to facilitate insertion of the polynucleotide into an appropriate vector.

"Sticky ends" are the single stranded nucleotide sequences recognized by a restriction endonuclease. When a certain vector is deemed suitable for expression of the pre-coelenterazine peptide, its restriction sites are identified. Sequences homologous to these restriction sites are generated on the 5' and 3' termini of the cDNA by PCR. Typically the restriction sites chosen fall outside the coding sequence, 5' or 3' of it. However, in some cases, a vector may provide a restriction sequence which falls quite near the start or stop codon, even within the coding sequence. When this occurs, introduction of the "sticky ends" may incorporate silent mutations or extra nucleotides into the coding sequence, and so cause the cDNA to encode for a slightly different sequence or number of bases. In the latter case, the cDNA may encode for additional amino acids in the pre-coelenterazine peptide.

Figure 1:
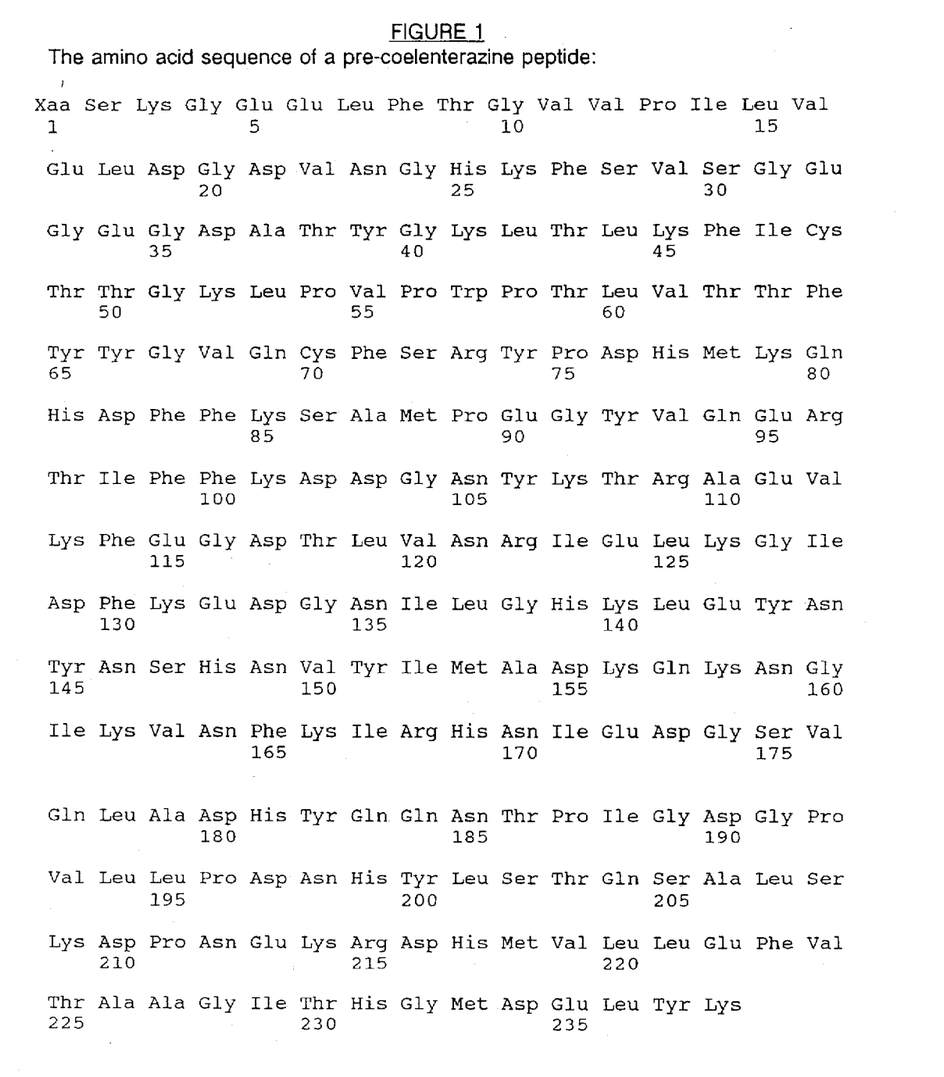
FIG. 1 is the amino acid sequence of one pre-coelenterazine peptide SEQ. ID No. 1.

For purposes of this disclosure, additional amino acid residues in the pre-coelenterazine peptide are indicated, not by altering the numbering of residues, but by considering the extra residues as one with either $R^1$ or $R^{238}$. Thus, in the peptide illustrated in FIG. 1, where $R^1$ is Xaa (an undefined amino acid), Xaa represents methionyl-alanine.

Conversely, when one or more amino acid residues are deleted due to the introduction of restriction sites in the cDNA, the amino acid residues are numbered according to the number they would have held in GFP. Thus, if $R^1$ through $R^3$ were omitted, the N-terminal Gly would nevertheless be numbered $R^4$ in the truncated peptide.

All of these pre-coelenterazine peptides may be synthesized by a suitable method such as by exclusive solid phase techniques, by partial solid-phase techniques, by fragment condensation or by classical solution phase synthesis. For example, the techniques of exclusive solid-phase synthesis are set forth in the textbook "Solid Phase Peptide Synthesis", J. M. Stewart and J. D. Young, Pierce Chem. Company, Rockford, 111, 1984 (2nd. ed.), and M. Bodanszky, "Principles of Peptide Synthesis", SpringerVerlag, 1984. The peptides may suitably be prepared using solid phase synthesis, such as that generally described by Merrifield, J. Am. Chem. Soc., 85, p. 2149 (1963), although other equivalent chemical syntheses known in the art may also be used as previously mentioned.

Alternatively, each of these peptides may be made using recombinant DNA techniques. This may be done, for example by generating a polynucleotide which encodes, according to the genetic code of chromosomal DNA, the amine acid sequence of the desired pre-coelenterazine peptide. This polynucleotide, introduced into an expression vector, may be expressed in vitro or in vive. The polynucleotide may be generated by procedures well known in the art, e.g., by DNA or RNA synthesis techniques and/or devices or by introducing one or more point mutations into the gene for GFP. Other suitable methods for this and other recombinant DNA techniques are discussed in Maniatis, *Molecular Cloning: A laboratory manual*, 2nd Ed., Cold Spring Harbor Laboratory Press (1989).

The invention further concerns a peptide derived from the pre-coelenterazine peptide in which one or both $R^{65}$ and $R^{66}$ are dehydroTyr. This peptide may be generated by synthesizing the pre-coelenterazine peptide in vivo.

B. POLYNUCLEOTIDE ENCODING THE PRE-COELENTERAZINE PEPTIDE

In a second embodiment, the invention provides a polynucleotide comprising one or more sequences of nucleotide bases collectively encoding the modified amino acid sequence of a GFP of *A. victoria* in which $R^{65}$ is Tyr.

The polynucleotide may also be comprised of one or more sequences of nucleotide bases collectively encoding the modified amino acid sequence of a GFP of *A. victoria* in which $R^{65}$ is Tyr, and further, in which $R^{80}$ may be Gln or Arg, $R^{100}$ may be Phe or Tyr, $R^{108}$ may be Thr or Ser, $R^{141}$ may be Leu or Met, $R^{172}$ may be Glu or Lys, and $R^{219}$ may be Val or Ile. Two suitable polynucleotides comprise one or more sequences of nucleotide bases collectively encoding for such a pre-coelenterazine in which $R^{80}$ is Gln, $R^{100}$ is Phe, $R^{108}$ is Thr, $R^{141}$ is Leu, $R^{172}$ is Glu, and $R^{219}$ is Val; or in which $R^{80}$ is Gln, $R^{100}$ is Tyr, $R^{108}$ is Ser, $R^{141}$ is Met, $R^{172}$ is Glu and $R^{219}$ is Ile.

These polynucleotides may be composed of either DNA or RNA, and may be either single or double stranded.

These polynucleotides may have, in its one or more sequences collectively encoding the pre-coelenterazine peptide, any nucleotide sequence which encodes one of the pre-coelenterazine peptides under the chromosomal genetic code. This code is degenerate; thus, the Arg at residue 109 may be encoded by nucleotide bases as CGT, but could, under the code, equally be CGC, CGA, CGG, AGA or AGG, and still encode for Arg. Similarly, nucleotide bases encoding Tyr as TAT could equally be TAC and still encode Tyr for residue 65 in the peptide. Alternatively, the polynucleotide may be a cDNA (or RNA equivalent) which includes, in addition to the nucleotides for $Ser^{65}$ being altered from TCT to TAT, mutations encoding for $R^{80}$ may be Gln or Arg, $R^{100}$ may be Phe or Tyr, $R^{108}$ may be Thr or Ser, $R^{141}$ may be Leu or Met, $R^{172}$ may be Glu or Lys, and $R^{219}$ may be Val or Ile. Thus, for example, the polynucleotide may include one or more of the following base mutations: the bases encoding $Gln^{80}$ may be altered from CAG (for Gln) to CGG (for Arg); the bases encoding $Phe^{100}$ may be altered from TTC to TAC (Tyr); bases for $Thr^{108}$ may be altered from ACA to AGA (for Ser); bases for $Leu^{141}$ may be altered from CTG to ATG (for Met); bases for $Gln^{172}$ may be altered from GAA to AAA (for Lys). All these polynucleotides which encode for the pre-coelenterazine peptides are found, upon expression, to direct the synthesis of one of the pre-coelenterazine peptides, and hence are embraced in the invention.

To generate a polynucleotide having these encoding sequences, one may introduce one or more point mutations into the cDNA for the GFP of *A. victoria* in the cDNA described in Prasher, et al., supra, using in vitro mutagenesis methods well known to those skilled in the art. If desired, one may make further mutations to effect changes at the nucleotides encoding amino acid residues 80, 100, 108, 141 and 219 as desired.

Figure 2:
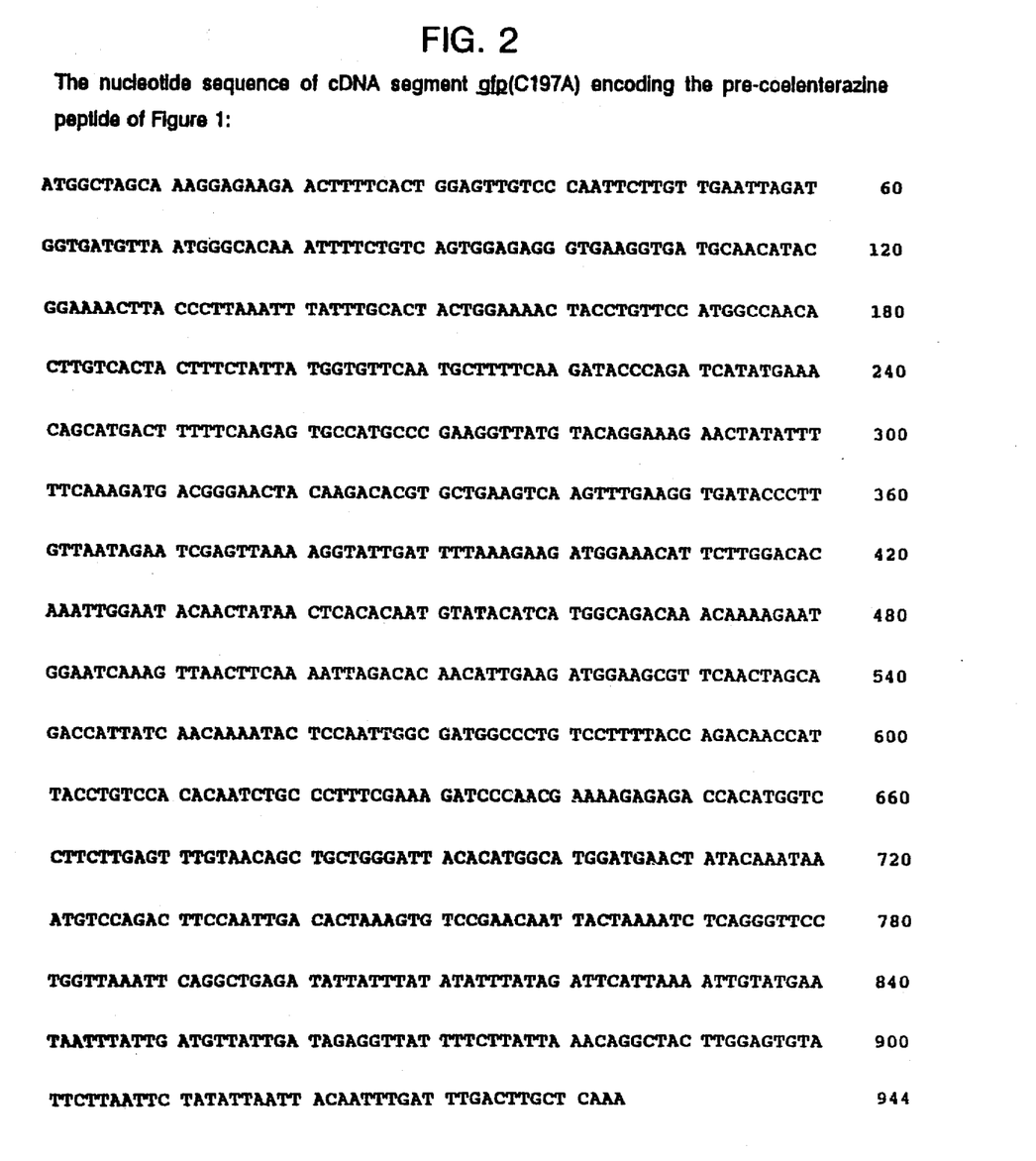
FIG. 2 is the nucleotide sequence SEQ. ID NO. 2 of cDNA segment gfp(C197A), in which nucleotides 1 through 717 encode the amino acids of the pre-coelenterazine peptide of FIG. 1.

The abbreviation gfp(C197A) is used herein to designate the cDNA encoding the modified *A. victoria* GFP having an amino acid sequence in which nucleotide 197 has been mutated from C to A. This cDNA encodes for the modified GFP illustrated in FIG. 1 having Tyr as $R^{65}$ in place of Ser gfp(C197A) is illustrated in FIG. 2, where bases 1 through 717 are encoding bases; the mutated base 197 is A; and the triplet codon formed by bases 718 through 720 form the stop codon.

All of the above polynucleotides may further comprise, 5' of said one or more sequences of bases, one or more appropriate regulatory control sequences which collectively enable expression of said one or more sequences of bases encoding said pre-coelenterazine peptide.

Suitably, the regulatory element may be a promoter. Suitable promoter elements include a promoter activated by heavy metal (e.g. the one described in Freedman, et el. *J. Biological Chemistry*, 268: 2554, 1993, incorporated herein by reference); a P 450 promoter (e.g. the cytochrome P 450); or a promoter for a stress protein, (e.g., described in Stringham, et. el., *Molecular Biology of the Cell*, 3: 221, 1992), one of said stress proteins being a heat-shock protein. Other suitable promoters include that of the arabinose operon (phi 80 dara) or the colicin E1, galactose, alkaline phosphatase or tryptophan operons. Similarly the ADH system may be employed to provide expression in yeast. Alternatively, the regulatory element may be an enhancer.

The regulatory control sequences are operatively linked with the polypeptide comprising one or more sequences of nucleotide bases collectively encoding an amino acid sequence of a pre-coelenterazine peptide; i.e., the regulatory control sequences are placed on the polynucleotide at a distance 5' of the one or more sequences suitable to enable expression of the sequences.

Polynucleotides which bear one or more of such regulatory control sequences may be used in transforming organisms, as when suitably the polynucleotide is included in an expression vector. The regulatory control sequences are selected for compatibility with the organism into which the polynucleotide is to be incorporated by transformation, i.e., the regulatory control sequences are those which may be recognized by the transformed organism or cell and which will aid in controlling the expression of said polynucleotide in the transformed organism.

Thus when the organism to be transformed is *E. coli*, the regulatory control sequence may be a promoter (e.g., the T7, the SP6 or lac promoter); or transcription initiation sequences for ribosome binding (e.g. the Shine-Delgarno sequence and the start codon AUG). When the organism to be transformed is eucaryotic, the regulatory control sequences may include a heterologous or homologous promoter for RNA polymerase II and/or a start codon AUG. For example, when the target of transformation is a mammalian cell, the regulatory control sequence may be a promoter (e.g. the SP 40 or the bovine papilloma virus promoter). Suitable regulatory control sequences for use in other microbe, or in animal, or plant cells may be selected according to criteria well known to persons having skill in the art. All of these regulatory control sequences may be obtained commercially (individually or incorporated into a vector) or assembled by methods well known in the art.

Where the polynucleotide carries one or more appropriate regulatory control sequences, there may further be present one or more further sequences of bases which collectively confer resistance to an antibiotic when the polynucleotide is expressed in an organism. Such genes for antibiotic resistance are desirable components for expression vectors since they facilitate identification of transformed cells grown in the presence of antibiotics, and exert a continual pressure on the transformed organisms to retain and express the expression vectors.

One polynucleotide suitable for use in transforming bacteria *E. coli* is plasmid TU#132.

All of the above polynucleotides may be synthesized by known methods. The polynucleotide may be generated by procedures well known in the art, e.g., by DNA or RNA synthesis techniques and/or devices or by introducing one or more point mutations into the gene for GFP. Other suitable methods for this and other recombinant DNA techniques are discussed in Maniatis, supra.

Thus one may use a DNA synthesizing device to construct the entire polynucleotide or to synthesize several fragments of a polynucleotide and ligate these together. This is a laborious process for polynucleotides, and thus it is usually preferable to generate polynucleotides by other means.

The present invention further includes a polynucleotide comprising one or more sequences of nucleotide bases collectively encoding the amino acid sequence of $R^1$ through $R^{69}$ of the pre-coelenterazine peptide, as well as an oligonucleotide comprising nucleotide bases encoding the sequence of amino acid residues 64 through 69 of the pre-coelenterazine peptide. One such oligonucleotide has the nucleotide sequence TTC TAT TAT GGT GTT CAA. Such poly- and oligonucleotides are useful as probes for homologous sequences of DNA or RNA. The attachment of a chemical label to such probes facilitates locating the probes in a test system. Suitable labels include radioisotopes (e.g. $^{32}P$, $^{35}S$, $^{125}I$), fluorescent compounds, or other well known labels (e.g. biotin) covalently linked to the poly- or oligonucleotide.

Although probes are normally used with a detectable label that allows easy identification, these poly- and oligonucleotides are also useful in unlabeled form, both as precursors of labeled probes and for use in methods that provide for direct detection of double-stranded DNA or DNA/RNA.

C. ORGANISMS TRANSFORMED WITH POLYNUCLEOTIDE ENCODING PRE-COELENTERAZINE PEPTIDE

A third embodiment of the present invention is an organism transformed with a polynucleotide comprising one or more sequences of nucleotide bases collectively encoding the modified amino acid sequence of a GFP of A. victoria in which $R^{65}$ is Tyr, $R^{80}$ is Gln or Arg, $R^{100}$ is Phe or Tyr, $R^{108}$ is Thr or Ser, $R^{141}$ is Leu or Met, $R^{172}$ is Glu or Lys, and $R^{219}$ is Val or Ile. Organisms which may suitably be transformed with such polynucleotides include bacterial cells (aerobic or anaerobic), yeast cells, fungal cells, insect cells, nematode cells, plant or animal cell. Suitable animal cells include, but are not limited to Vero cells, HeLa cells, Cos cells, CV1 cells and various primary mammalian cells.

Transformation of these cells may be performed by techniques well known to persons having skill in the art. Thus, for instance, transformation of yeast and plant cells must be preceded by treatment of the cells to remove the rigid cell wall, as by treatment with a digestive enzyme; the resulting spheroplasts and chloroplasts readily take up polynucleotide plasmids and upon return to growth medium regenerate their cell walls.

One transformed organism is E. coli SMC2, an E. coli of the Strain BL21 (DE3)Lys S which has been transformed with Plasmid TU#132. It is believed that plasmid TU#132 and E. coliSMC2, deposited on Feb. 4, 1994 with the American Type Culture Collection (ATCC), 12301 Parklawn Drive, Rockville, Md. 20852, USA, under the provision of the Budapest Treaty for the International Recognition of the Deposit of Microorganisms for the Purposes of Patent Procedure and Title 37 Section 1.801 et seq. of the Code of Federal Regulations, and accorded ATCC Accession No. 755666 and ATCC Accession No. 69553 respectively, are a plasmid carrying a cDNA encoding for a pre-coelenterazine peptide, and an E. coli of Strain BL21 (DE3)Lys S transformed with such a plasmid.

It is noted that the deposited material is not considered to be essential to the practice of the claimed invention and that the grant of admission to the depository to distribute samples of the biological material does not constitute an express or implied license to practice the invention claimed in any patent issuing from the instant application or from any continuation, divisional or reissue application thereof.

D. METHOD OF SYNTHESIZING PRE-COELENTERAZINE AND COELENTERAZINE

The fourth embodiment of the present invention comprises a method of synthe-sizing a pre-coelenterazine peptide comprising a modified A. victoria GFP having an amino acid sequence in which $R^{65}$ is Tyr. The method comprises incubating a polynucleotide comprising one or more sequences of nucleotide bases collectively encoding an amino acid sequence of such a peptide in the presence of means for effecting expression of the polynucleotide under conditions favorable for the express-ion of the polynucleotide. These means may be an in vitro transcription/translation system or an organism transformed with the polynucleotide.

In this method, the means for effecting expression of the polynucleotide may be either an in vitro cell-free translation system or an organism which has been transformed with the polynucleotide, being viable and in a medium containing assimilable sources of carbon, nitrogen, and inorganic substances. One suitable means for effecting expression in vivo is E. coliSMC2.

When the means for effecting expression is such a transformed organism, the polynucleotide may comprise one or more appropriate regulatory control sequences, and one or more sequences of bases which collectively confer resistance to an antibiotic upon the transformed organism. One suitable polynucleotide is Plasmid TU#132.

There is further provided a method of synthesizing coelenterazine comprising synthesizing the pre-coelenterazine peptide according to the above method and isolating coelenterazine from the means for effecting expression of the polynucleotide.

In this method, the means for effecting expression may be an organism capable of expressing the polynucleotide, i.e., one transformed or transformable with the polynucleotide when subjected to conditions favorable to transformation in the presence of the nucleotide. The transformed organism and the transformable organism (once the latter is transformed) is cultured for one or more generations under conditions favorable to growth of said organism and to expression of the polynucleotide. In this method, the step of isolating coelenterazine is performed by lysing the progeny of said cultured transformed cells to form a cell-free extract, and isolating coelenterazine from said extract.

Coelenterazine is a highly labile substance in aqueous based media with a half-life of one to two hours. When it is suspended in methanolic HCl, however it is stable, even at room temperature. Accordingly, the step of isolating coelenterazine from said extract may be performed by adding methanolic HCl to the cell lysate, mixing and removing the suspended cell solids.

It is well known that coelenterazine may be stabilized in aqueous media by being modified from its keto form (Formula III) to its enol form in luciferyl sulfate. The enol sulfate form of coelenterazine has conventionally been termed luciferyl sulfate and this term is employed herein. Luciferyl sulfate has the structure shown in Formula V:

Formula V

This modification to luciferyl sulfate is carried out by incubating coelenterazine with the enzyme luciferin sulfokinase and 3',5'-diphosphoadenosine. The conversion of luciferyl sulfate to luciferin is 3,5-diphosphoadenosine-linked. This may be accomplished by incubating the isolated coelenterazine with a compatible luciferin sulfokinase, suitably a luciferyl sulfokinase derived from a coelenterate such as *Renilla reniformis*. Methods well known in the art may be used to isolate and purify luciferyl sulfokinase, e.g., methods described in Cormier et al., *Cell. Physiol*, 81, No. 2,291–297 (1973), incorporated herein by reference; Hori et al., *Biochim. Biophys. Acta* 256:638–644 (1972), incorporated herein by reference; and Karkhanis and Cormier, *Bioch.* 10:317–326 (1971), incorporated herein by reference. Luciferin sulfokinase may be isolated from this organism according to the procedures described in Cormier et el., *Bioch.* 9 1184–1189, 1970, incorporated herein by reference.

Purification of the coelenterazine from the lysate may be accomplished using chromatography procedures well known in the art. Such procedures include size exclusion chromatography, column chromatography and high performance HPLC using one or more reverse phase HPLC procedures. Combinations of such chromatography methods may also be employed. In this manner coelenterazine is obtained in purified form.

Coelenterazine synthesized by these methods may be characterized by one or more of the following methods: HPLC, emission spectroscopy, and mass spectroscopy. Performance of these tests upon coelenterazine synthesized according to the above methods demonstrates that the coelenterazine has the same chromatographic profile as natural coelenterazine; that the synthetic coelenterazine emits blue light at 480 nm; and that it has a mass spectroscopy profile nearly identical to that of natural coelenterazine.

Accordingly, in a further embodiment of the invention, there is provided purified coelenterazine and luciferyl sulfate made by the above methods. The production process of these compounds is carried out in a conventional manner. Transformed bacterial cells are resuspended in a suitable known buffer solution, followed by lysing the bacterial cells in a conventional manner such as ultrasonic wave treatment and/or enzyme treatment, and obtaining the supernatant by means of centrifugation.

HPLC. A Bio-Rad ODS-5S reverse-phase HPLC column (4×250 mm) may be used. High-performance liquid chromatography may be carried out on Waters 600 multisolvent system with Waters 490 programmable wavelength detector and Waters 740 data module. Column eluent is monitored at three wavelengths simultaneously so as to detect coelenterazine and UV absorption contamination in real time. All HPLC runs were performed in acidic methanolic buffer solutions, so the coelenterazine is always in the 370 nm-absorbing form.

Photometric Determination. Bioluminescense may be measured and peak light intensitites determined, with a luminometer. Bioluminescensce intensity is converted to quanta per second by calibrating the instrument relative to a radioactive $^{14}C$ light standard that emits maximally in the 410 nm region. Routine assays for coelenterazine are performed by rapidly injecting 10 μl of clarified *E. coli* SMC2 cell extract in methanolic-HCl into a vial containing Renilla luciferase in 1 ml of luciferase buffer.

Analytical Spectra. A Cary 17-D recording spectrophotometer and a Bausch and Lomb Spectronic 2000 are used interchangeably for fixed-wavelength absorbance measurements or for spectral scans.

Mass Spectroscopy. Coelenterazine isolated from recombinant bacteria may be analyzed by electrospray ionization mass spectrometry and liquid secondary ion mass spectrometry followed by mass spectrometry/mass spectrometry. This will provide molecular weight and structural information on the isolated coelenterazine. These two tools also provide information on the purity of the cyclic tripeptide as well as of other peptides, if present.

E. IMPROVED ASSAY FOR DETECTING MUTAGENESIS

In another embodiment, the invention provides an organism transformed with two polynucleotides, one comprising one or more sequences of nucleotide bases collectively encoding an amino acid sequence for a luciferase peptide compatible with coelenterazine. The second polynucleotide comprises one or more sequences of bases collectively encoding the amino acid sequence of said pre-coelenterazine peptide.

One of these polynucleotides has a mutation which prevents its expression product from having a bioluminescent interaction with any coelenterazine. This mutation, which may suitably be an insertion, a duplication, a translocation, mis-sense, or a reading shift mutation, is desirably reversible upon exposure to a mutagen. Thus, should exposure to a mutagen reverse the mutation in the second polynucleotide, the organism will express the first and second polynucleotides, thus generating coelenterazine and an active luciferase compatible therewith.

Since reversal of the mutation results in bioluminescence, the organism may be employed in a mutagenesis assay. Therefore, the invention further provides a method of testing the mutagenicity of a chemical compound, comprising: a) transforming a population of organisms with said first and said second polynucleotides; b) growing a culture of said transformed organisms through one or more generations in a nutrient medium comprising said chemical compound; and c) measuring the bioluminescence of said culture and comparing said bioluminescence to that from a culture of non-transformed mutagenized control organisms.

In this method, the rate of mutagenesis may be measured instrumentally, as by subjecting said mutagenized cultures to on-line luminometry, avoiding the Ames test steps of preparation of agar plates and tedium of scoring bacterial colonies on the plates.

In order to halt the growth of non-revertant organisms while performing this method, and to prevent "crowding out" of revertant growth by non-revertants, the expression of coelenterazine and luciferase may be linked to mutant survival. This may suitably be done by placing the mutation on a regulatory sequence controlling the expression of the transformed organisms' antibiotic resistance or the synthesis of an obligatory co-factor. Suitable locations for such a mutation include the promotor region or the region of repressor binding.

The invention now being fully described, it will be apparent to one of ordinary skill in the art that many changes and modifications may be made thereto without departing from the spirit or scope of the invention as set forth herein.

EXAMPLE I

In vitro MUTAGENESIS

TU#58 (described in U.S. patent application Ser. No 08/119, 678) is treated with NcoI and EcoRI to generate a fragment of the GFP gene. This fragment is replicated by PCR with an oligomeric primer to insert the C197A mutation. The fragment is also treated with primers (NcoI at 5', T3 at 3') to incorporate restriction sites. The primer which incorporates the C197A mutation has the sequence (SEQ. ID No. 4):

CCT GTT CCA TGG CCA ACA CTT GTC ACT ACT TTC TAT TAT G

The "A" base six bases upstream of the 3' end is the nucleotide which effects the C197A mutation.

The replicated fragment containing these mutations is then hybridized and ligated to TU#58 which has been treated with NcoI and EcoRI to produce plasmid TU#132. Sequencing of plasmid TU#132 confirms the incorporation of both endonuclease sites and of the C197A mutation.

EXAMPLE II

In vitro MUTAGENESIS

An alternative method of generating a point mutation to that set out in Example I is as follows. A synthetic oligonucleotide is used to introduce the mutation. The synthetic oligonucleotide may be synthesized employing a commercially available automatic DNA synthesis apparatus, the product being subject to end-phosphorylation in a conventional manner to obtain a primer.

The oligomer is hybridized to the single strand plasmid TU#132 disclosed in U.S. patent application Ser. No. 08/119,678 under conditions of low stringency, and subjected to three-stage treatment: treatment at 1000° C. for 5 minutes, followed by allowing the resulting material to stand at 30° for 3 minutes and further at 4° C. for 30 minutes to carry out annealing and reacting dXTP (X=G, A, T, C) with Klenow fragment (E. coli polymerase) in the presence of T4-ligase to prepare a duplex chain.

EXAMPLE III

TRANSFORMATION

E. coli of strain BL21 (DE3)Lys S is transformed with plasmid TU#132. Transformants are selected on media containing ampicillin (100/µg/ml) and IPTG (0.8 mM). Plasmid DNA is isolated from the tranformants and analyzed by automated sequence analysis, which confirms the presence of the C197A mutation.

EXAMPLE IV

MEASUREMENT OF COELENTERAZINE SYNTHESIZED IN E. coli SMC2

The bioluminescense of coelenterazine synthesized by E. coli SMC2 cultivated as in the preceding Example is measured on a custom built luminometer. The circuitry of this luminometer is modeled after that described in Blinks et al., Methods in Enzymol., 57 292–328, 1978, incorporated herein by reference; the reaction chamber and shutter assembly of the luminometer are modeled after that described in Levine and Ward, Comp. Bioch. Physiol. 72B, 77–85 1982, incorporated herein by reference.

The column is equilibrated with a starting buffer of 0.1% trifloracetic acid at a flow rate of 1 mL/min. Coel-enterazine-containing samples are injected onto the column in starting buffer. Five minutes after sample injection, a linear methanol gradient (+1% methanol/min, flow rate 1 mL/min) is initiated until all components in the mixture are eluted. Following each HPLC run, the column is rinsed with 100% methanol. Under these conditions, coelenterazine elutes at 90% methanol.

Peak light intensities of the coelenterazine are determined on this lumino-meter and bioluminescensce intensity is converted to quanta per second by cali-brating the instrument relative to a radioactive $^{14}C$ light standard that emits maximally in the 410 nm region.

A paste of E. coli SMC2 grown as in Example IV is lysed by sonication in absolute methanol acidified to 1N with HCl. 10 µl of clarified E. coli SMC2 cell extract in methanolic-HCl is rapidly injected into a vial containing Renilla luciferase in 1 ml of luciferase buffer. The coelenterazine luciferase assay buffer described in Matthews et al., Bioch. 16 85–91, 1977) incorporated herein by reference is prepared. 50 µl of pure luciferase (prepared as described in Matthews et al., supra) is added to the vial. Corrected emission spectra are collected on an on-line computerized fluorimeter.

Figure 3:
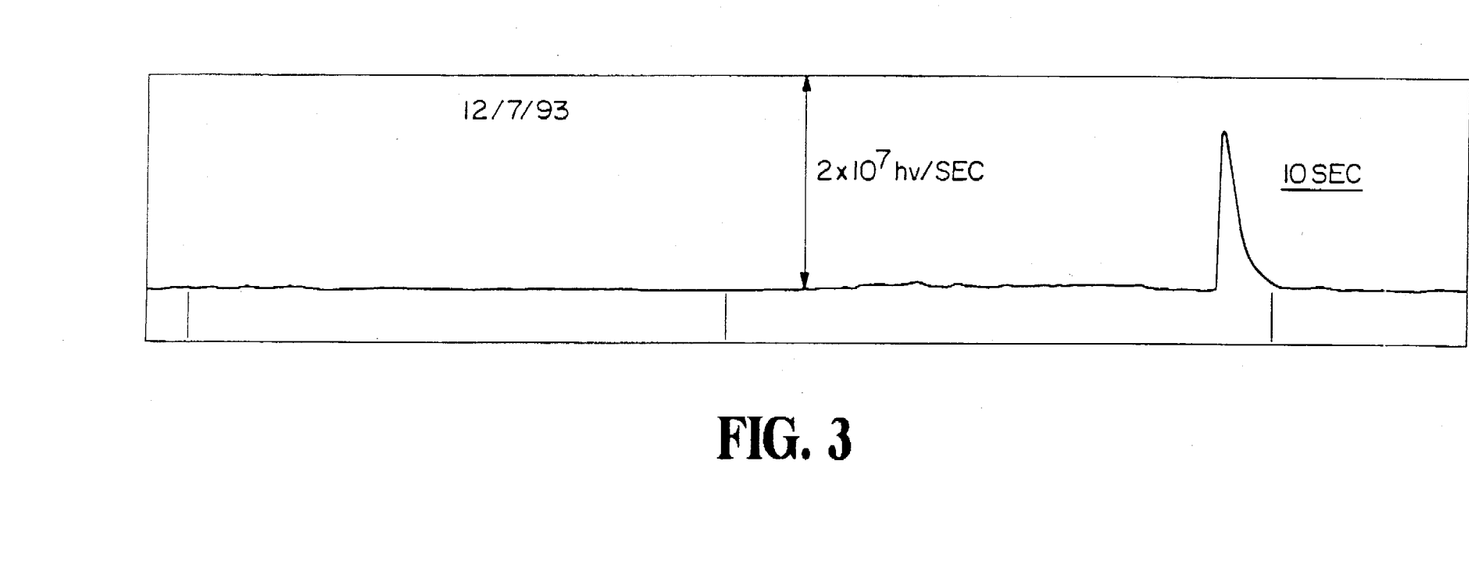
FIG. 3 is the print out of a luminometry test of coelenterazine isolated from *E. coli* SMC2.

The luminometer gives a reading of $1.5 \times 10^7$ hv/sec upon addition of luciferase, against a background of $4 \times 10^5$ hv/sec. The read-out from this instrument appears in FIG. 3.

---

We claim:

1. A method of synthesizing coelenterazine comprising:

a) synthesizing a pre-coelenterazine peptide comprising a modified amino acid sequence of a green-fluorescent protein of *A. victoria* in which $R^{65}$ is Tyr, said method comprising incubating a polynucleotide in the presence of means for effecting expression of said polynucleotide under conditions favorable to expression of said polynucleotide, said polynucleotide comprising one or more sequences of nucleotide bases collectively encoding said pre-coelenterazine peptide, wherein said one or more sequences of bases collectively encoding said amino acid sequence of said pre-coelenterazine peptide are uninterrupted by non-coding sequences; and b) isolating coelenterazine from said means.

2. The method of claim 1, wherein said step of incubating said polynucleotide is preceded by transforming an organism with said polynucleotide; wherein said means for effecting expression of said polynucleotide is said transformed organism, wherein said step of incubating said polynucleotide in the presence of said means is performed by culturing said transformed organism for one or more generations under conditions favorable to growth of said transformed organism and to expression of said polynucleotide; and wherein said step of isolating coelenterazine is performed by lysing the progeny of said cultured transformed organism to form a cell-free extract, and isolating coelenterazine from said extract.

3. The method of claim 2 wherein means for effecting expression of said polynucleotide is *E. coli* strain BL21 (DE3)Lys S transformed with an expression vector comprising, 5' of said one or more sequences of nucleotide bases collectively encoding the amino acid sequence of pre-coelenterazine peptide, one or more appropriate regulatory control sequences which collectively enable expression of said polynucleotide; and one or more sequences of bases which collectively confer resistance to an antibiotic upon an organism.

4. The method of claim 3 wherein said means for effecting expression of said polynucleotide is the *E. coli* SMC2 (ATCC Accession No. 69553).

5. The method of claim 1 further comprising the step of converting isolated coelenterazine to luciferyl sulfate.

6. The method of claim 5 wherein the step of converting coelenterazine is performed by incubation of said isolated coelenterazine with a luciferin sulfokinase.

7. The method of claim 6 wherein said luciferin sulfokinase is derived from the organism *Renilla reniformis*.

* * * * *

UNITED STATES PATENT AND TRADEMARK OFFICE
CERTIFICATE OF CORRECTION

PATENT NO. : 5,741,668
DATED : April 21, 1998
INVENTOR(S) : William Ward and Martin Chalfie It is certified that error appears in the above-identified patent and that said Letters Patent is hereby corrected as shown below:

In the Title:
    Correct the Title to read as follows:

A BIOLUMINESCENT INDICATOR FOR GENE EXPRESSION AND DETECTION OF MUTAGENSIS BASED UPON THE EXPRESSION OF A GENE FOR A MODIFIED GREEN_FLUORESCENT PROTEIN

Signed and Sealed this

Eighth Day of September, 1998

*Attest:*

BRUCE LEHMAN

*Attesting Officer*      *Commissioner of Patents and Trademarks*